(12) United States Patent
Cotrell

(10) Patent No.: US 9,833,396 B2
(45) Date of Patent: Dec. 5, 2017

(54) PERSONAL CARE COMPOSITION

(71) Applicant: Innospec Limited, Chesire (GB)

(72) Inventor: Philip Cotrell, Edison, NJ (US)

(73) Assignee: INNOSPEC LIMITED, Chesire (GB)

( * ) Notice: Subject to any disclaimer, the term of this patent is extended or adjusted under 35 U.S.C. 154(b) by 0 days.

(21) Appl. No.: 15/154,129

(22) Filed: May 13, 2016

(65) Prior Publication Data

US 2017/0095411 A1    Apr. 6, 2017

Related U.S. Application Data

(63) Continuation of application No. 12/742,834, filed as application No. PCT/GB2008/051071 on Nov. 17, 2008, now abandoned.

(30) Foreign Application Priority Data

Nov. 16, 2007    (GB) .................................. 0722550.1

(51) Int. Cl.
| | |
|---|---|
| *A61K 8/46* | (2006.01) |
| *A61Q 5/02* | (2006.01) |
| *A61Q 5/12* | (2006.01) |
| *A61Q 19/00* | (2006.01) |

(52) U.S. Cl.
CPC .............. *A61K 8/466* (2013.01); *A61Q 5/02* (2013.01); *A61Q 5/12* (2013.01); *A61Q 19/00* (2013.01)

(58) Field of Classification Search
None
See application file for complete search history.

(56) References Cited

U.S. PATENT DOCUMENTS

| | | |
|---|---|---|
| 4,954,282 A | 9/1990 | Rys et al. |
| 5,132,037 A | 7/1992 | Greene et al. |
| 5,393,466 A | 2/1995 | Ilardi et al. |
| 5,556,628 A | 9/1996 | Derian et al. |
| 5,612,307 A | 3/1997 | Chambers et al. |
| 5,661,189 A | 8/1997 | Grieveson et al. |
| 5,965,500 A | 10/1999 | Puvvada |
| 6,077,816 A | 6/2000 | Puvvada et al. |
| 6,150,312 A | 11/2000 | Puvvada et al. |
| 6,174,846 B1 | 1/2001 | Villa |
| 2003/0049292 A1 | 3/2003 | Turowski-Wanke et al. |
| 2003/0180246 A1 | 9/2003 | Frantz et al. |
| 2004/0202636 A1 | 10/2004 | Kaczvinsky, Jr. et al. |
| 2005/0089536 A1 | 4/2005 | Loffler et al. |
| 2006/0270584 A1* | 11/2006 | Frantz ..................... A61K 8/44 510/424 |

FOREIGN PATENT DOCUMENTS

| | | |
|---|---|---|
| WO | 94/03152 | 2/1994 |
| WO | 94/09763 | 5/1994 |
| WO | 03055456 A1 | 7/2003 |
| WO | 03074020 A1 | 9/2003 |
| WO | 2005075623 | 8/2005 |
| WO | 2005094781 A1 | 10/2005 |
| WO | 2007003289 A1 | 1/2007 |
| WO | 2007130390 A3 | 11/2007 |
| WO | WO 2007130390 A2 * | 11/2007 ............. A61K 8/466 |

OTHER PUBLICATIONS

International Preliminary Report on Patentability from foreign parent Application No. PCT/GB2008/051071, filed on Nov. 17, 2008, dated, Nov. 16, 2007.
The Written Opinion of the International Searching Authority from foreign parent Application No. PCT/GB2008/051071 filed on Nov. 17, 2008, dated, Nov. 16, 2007.

* cited by examiner

*Primary Examiner* — Frederick Krass
*Assistant Examiner* — Michael P Cohen
(74) *Attorney, Agent, or Firm* — Stout, Uxa & Buyan, LLP; Carlos A. Fisher

(57) ABSTRACT

An aqueous shear-thinning personal care composition comprises: (a) at least 3 wt % of a sulfonate compound of general formula (I): where $R^1$ represents a $C_{8-22}$ alkyl group alkyl group; $R^2$ represents a $C_{1-4}$ alkyl group; each of $R^3$, $R^4$ and $R^5$ independently represents a hydrogen atom or a $C_{1-4}$ alkyl group; and $M^+$ represents a sodium or potassium cation; (b) at least 3 wt % of an amphoteric or zwitterionic surfactant; (c) at least 10 wt % of water; and (d) at least 0.5 wt % of an additional component in the form of particles or droplets suspended in the composition. The composition is stable in an aqueous environment and can be formulated with a wide range of additional components.

18 Claims, 3 Drawing Sheets

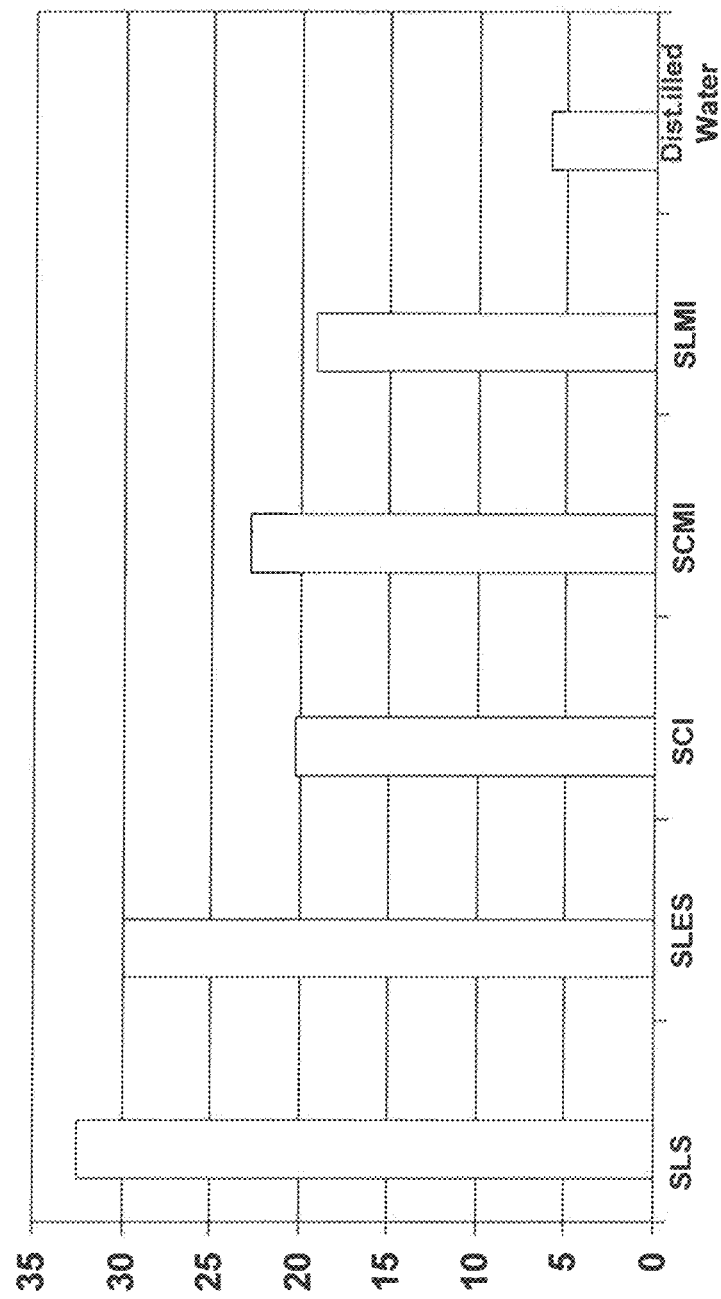

PERSONAL CARE COMPOSITION

CROSS-REFERENCE TO RELATED APPLICATIONS

This application is a continuation of co-pending U.S. application Ser. No. 12/742,834, which is a U.S. national stage application under 35 U.S.C. 371 of International Application No. PCT/GB08/51071 filed Nov. 17, 2008 and entitled "COMPOSITION", which in turn claims priority to Great Britain Patent Application No. 0722550.1 filed Nov. 16, 2007, both of which are incorporated by reference herein in their entirety for all purposes.

This invention relates to a personal care composition, for example a liquid or gel body wash, shower gel, handwash, skin cream, hair conditioner or moisturiser.

U.S. Pat. No. 5,612,307 discloses an aqueous liquid cleansing and moisturising composition comprising: a) a surface active agent selected from anionic, nonionic, zwitterionic and cationic, surface active agents, soap and mixtures thereof; and b) a benefit agent; wherein the benefit agent and surface active agent are separate but combinedly dispensable from a single packaging means in a predetermined ratio as discrete domains, the domains having one dimension of at least about 1000 microns.

An advantage of the invention of U.S. Pat. No. 5,612,307 is said to be that it leads to improved deposition of benefit agents from a surface active agent containing aqueous liquid composition during use. The surface active agent and benefit agent are separated in the composition, i.e. they do not directly contact one another in the composition. This avoids adverse interactions which may occur between these two components and which may result in ineffective deposition of the benefit agent.

The composition of U.S. Pat. No. 5,612,307 is said to be suitable for cleansing and "moisturising", "conditioning" or "protection" of the skin. The benefit agent is included in the composition to moisturise, condition and/or protect the skin. By "benefit agent" is meant a substance that softens the skin (stratum corneum) and keeps it soft by retarding the decrease of its water content and/or protects the skin.

Preferred benefit agents of U.S. Pat. No. 5,612,307 include: silicones and siloxanes; fats and oils; waxes; hydrocarbons; higher fatty acids; higher alcohols; esters; essential oils; lipids; vitamins; sunscreens; and phospholipids.

Where adverse interactions between the benefit agent and surface active are likely to be particularly acute, U.S. Pat. No. 5,612,307 states that the benefit agent may be incorporated in the compositions in a carrier.

The surface active agent of U.S. Pat. No. 5,612,307 is preferably present at a level of from 1 to 35 wt %, preferably 3 to 30 wt %.

One preferred anionic detergent for use in the invention of U.S. Pat. No. 5,612,307 is a fatty acyl ethane sulfonate of formula $RCO_2CH_2CH_2SO_3M$, where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

It is also preferable in U.S. Pat. No. 5,612,307 that the composition includes from 0.5 to 15 wt % of a cosurfactant agent with skin-mildness benefits. Suitable materials are zwitterionic detergents identified in U.S. Pat. No. 5,612,307.

A favoured fatty acyl ethane sulfonate is "SCI" (sodium cocyl isethionate). SCI is commercially available and is a successful product but the scope it offers formulators is limited by its low solubility in water; its low hydrolytic stability, and the lack of stability in its pH value, over time.

The present invention is based on the use of a different fatty acyl sulfonate salt, and its advantageous co-formulation with amphoteric or zwitterionic surfactants, in aqueous environments.

In accordance with a first aspect of the present invention there is provided an aqueous shear-thinning personal care composition comprising:

(a) at least 3 wt % of a sulfonate compound of general formula $$R^1-\underset{\underset{}{\overset{\overset{O}{\|}}{C}}}{}-O-\underset{\underset{R^3}{|}}{\overset{\overset{R^2}{|}}{C}}-\underset{\underset{R^5}{|}}{\overset{\overset{R^4}{|}}{C}}-SO_3^-M^+$$

where $R^1$ represents a $C_{8-22}$ alkyl group;
$R^2$ represents a $C_{1-4}$ alkyl group;
each of $R^3$, $R^4$ and $R^5$ independently represents a hydrogen atom or a $C_{1-4}$ alkyl group; and
$M^+$ represents a cation;

(b) at least 3 wt % of an amphoteric or zwitterionic surfactant;
(c) at least 10 wt % of water; and
(d) at least 0.5 wt % of an additional component in the form of particles or droplets suspended in the composition.

There may be further components present in the composition. Percentages given herein are percentages on total weight of the composition, including any such further components, for example when there is a plurality of compounds (a); and/or a plurality of surfactants (b).

Many additional components are described hereafter, some of which may go into solution and some of which remain in the composition as particles or droplets. The stipulation of the definition of the invention is that there must be at least one additional component which is in the form of particles or droplets suspended in the composition. The compositions of the present invention have an exceptional ability to be formulated with further components and in particular to suspend particles or droplets and we regard this as an essential element of the invention.

Preferably $R^1$ represents a $C_{10-20}$ alkyl group, most preferably a $C_{12-18}$ alkyl group.

Preferably $R^2$ represents a $C_{1-4}$ alkyl group in which a propyl or butyl group is straight-chain. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group, Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

Preferably $M^+$ represents an ammonium cation or, most preferably, a metal cation. Suitable metal cations include alkali metal cations, for example sodium and potassium cations, and alkaline earth metal cations, for example calcium and magnesium cations. Preferably $M^+$ represents a potassium cation, or, especially, a sodium cation.

Of course, a plurality of compounds (a) may be present.

Component (b) may include amphoteric or zwitterionic surfactants selected from betaines, for example alkyl betaines, alkylamidopropyl betaines, alkylamidopropyl hydroxy sultaines, alkylampho acetates, alkylamphodiacetates, alkylamphopropionates, alkylamphodipropionates, alkyliminodipropionates and alkyliminodiacetate.

Of course, a plurality of surfactants (b) may be present.

Amphoteric or zwitterionic surfactants may include those which have an alkyl or alkenyl group of 7 to 22 carbon atoms and comply with an overall structural formula:

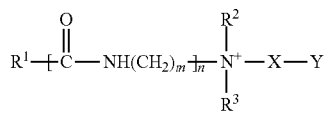

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Amphoteric or zwitterionic surfactants may include simple betaines of formula:

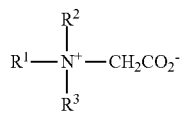

and amido betaines of formula:

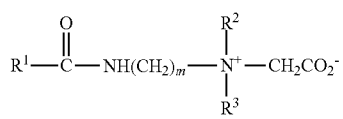

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Amphoteric or zwitterionic surfactants may include sulphobetaines of formula:

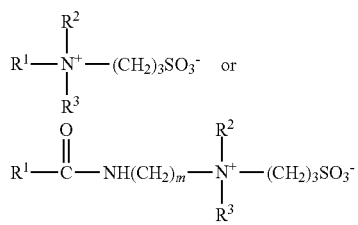

where m is 2 or 3, or variants of these in which $-(CH_2)_3 SO_3^-$ is replaced by

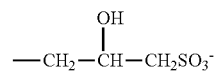

where $R^1$, $R^2$ and $R^3$ in these formulae are as defined previously.

Amphoteric or zwitterionic surfactants may include amphoacetates and diamphoacetates. Amphoacetates generally conform to the following formula:

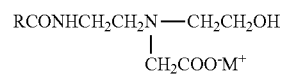

Diamphoacetates generally conform to the following formula:

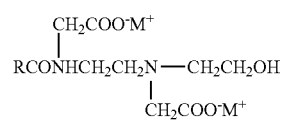

where R is an aliphatic group of 8 to 22 carbon atoms and M is a cation such as sodium, potassium, ammonium, or substituted ammonium.

Compounds such as oleylbetaine and cocoamidopropyl-hydroxy-sultaine are regarded as very safe for the human body and for the eyes. Also preferred in some embodiments are sodium lauroamphoacetate, sodium cocoamphoactetate, disodium lauroamphoacetate, and disodium cocoamphodiacetate.

Preferably, in a composition in accordance with the present invention, component (a) is present in an amount of up to 30% by total composition weight.

Preferably in a composition in accordance with the present invention, component (b) is present in an amount of up to 30% by total composition weight.

Preferably in a composition in accordance with the present invention, component (c) is present in an amount of from 20% to 95% by total composition weight, preferably from 50 to 90%.

In one embodiment the composition of the present invention is a free-flowing liquid.

In one embodiment a composition in accordance with the invention is a shear thinning composition.

A composition in accordance with the present invention may suitably have a viscosity of from 250 to 300,000 mPa·s, measured at 25° C. using a Brookfield rotational viscometer equipped with an appropriate spindle at a rotation speed of from 0.1 revolutions per minute (rpm) to about 60 rpm. Examples of appropriate spindles include the Brookfield RVT Viscometer Helipath T-Bar Spindles B and C (used in the examples which follow). At low shear rates (rotation speeds) the viscosity as measured may be up to 300,000 mPa·s. At high shear rates (rotation speeds) the viscosity as measured may be as low as 250 mPa·s.

The compositions of the invention may be pourable liquids or semi-liquids e.g.

The compositions of the invention may be soft gels and may suitably be of viscosity in the range 800 to 20,000 mPa·s, measured under the conditions stated above.

The compositions of the invention may be firmer gels and may be of viscosity in the range 3000 to 100,000 mPa·s, measured under the conditions stated above.

Surprisingly, the aqueous compositions of the invention have desirable non-Newtonian properties and excellent suspending properties, being capable of maintaining solid or non-solid water-insoluble particles or droplets in suspension. Under the conditions of testing which have been applied in relation to the invention, no sedimentation or separation whatsoever of the water-insoluble particles or droplets has developed over time. Furthermore the compositions of the invention produce an excellent rich creamy foam which is stable, and is mild to the skin and eyes.

Without being bound by theory, it is believed possible that the following microstructural conditions are achieved in the present invention.

The compositions of the present invention are believed to exhibit a so-called lamellar phase structure comprising spherulites in suspension.

By "lamellar phase" is intended a hydrated solid phase or a liquid crystal phase in which several double layers are arranged in a parallel network, separated by layers of water or of an aqueous solution. In respect of the spherulites, these are multilamellar vesicles comprising several layers of surface-active agents arranged concentrically and generally ranging from 0.1 to 50 microns in size.

More specifically, the corresponding phase structure may, we believe, be a birefringent solution, optically characteristic of a non-isotropic mesomorphic phase. By the term "water-insoluble particles" are intended solid or non-solid entities which are not solubilized in the aqueous medium of the subject composition. These, more particularly, are solid particles or suspended droplets.

However the more significant point is not the microstructure per se but the fact that the components together produce a composition with excellent overall or macroscopic properties.

Important advantages of the compositions of the invention over many other compositions, and in over particular over compositions containing fatty acyl ethane sulfonates, such as SCI, is that they are hydrolytically stable and pH-stable, and that they can be formulated with many further ingredients, including particulates and droplets, without adverse interactions being found.

The composition may contain an electrolyte. An electrolyte is suitably present in an amount of from 0.5% to 25%, preferably 1% to 15%, preferably 2 to 10%, by total composition weight. The concentration thereof may be adjusted to produce the desired formulation.

Suitable as an electrolyte are ionic compounds, for example metal salts selected from sodium chloride, sodium sulfate, potassium chloride, potassium sulfate, sodium phosphate, disodium phosphate, potassium phosphate, dipotassium phosphate, sodium isethionate, sodium methyl isethionate and sodium lactate; and non-metallic salts, for example sodium citrate, ammonium chloride, ammonium citrate and ammonium lactate.

Preferred electrolytes include sodium and ammonium chloride.

Said additional component (d) is suitably one or more benefit agents in the form of particles or droplets. By "benefit agent" we can adopt the definition of US 2003/0180246A, that is, a "benefit agent" is any active ingredient that is to be delivered into the skin or hair, or onto the skin or hair, or both, at a desired location. For example, a benefit agent may be a substance that softens the skin (stratum corneum) and keeps it soft by retarding the decrease of its water content; and/or a substance which protects the skin; and/or an exfoliating material, for example a water insoluble particulate or suspended abrasive.

Preferred benefit agents include:
a) silicone oils, gums and modifications thereof such as linear and cyclic polydimethylsiloxanes, amino, alkyl alkylaryl and aryl silicone oils;
b) fats and oils including natural fats and oils such as jojoba, soyabean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;
c) waxes such as carnauba, spermaceti, beeswax, lanolin and derivatives thereof;
d) hydrophobic plant extracts;
e) hydrocarbons such as liquid paraffins, petroleum jelly, microcrystalline wax, ceresin, squalene, squalane, and mineral oil;
f) higher fatty acids such as lauric, myristic, palmitic, stearic, behenic, oleic, linoleic linolenic, lanolic, isostearic and poly unsaturated fatty acids (PUPA) acids;
g) higher alcohols such as lauryl, cetyl, steryl, oleyl, behenyl, cholesterol and 2-hexadecanol alcohol;
h) esters (fatty acid esters, fatty alcohol esters) including cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;
i) essential oils such as fish oils, fragrance oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;
j) lipids such as cholesterol, ceramides, sucrose esters and pseudo-ceramides as described in European Patent Specification No. 556 957;
k) vitamins such as vitamin A and E, and vitamin alkyl esters, including those vitamin C alkyl esters;
l) sunscreens such as octyl methoxyl cinnamate (Parsol MCX) and butyl methoxy benzoylmethane (Parsol 1789);
m) phospholipids; and
n) one or more of scrubbing beads, anti-dandruff agents, anti-UV actives, mica, silica, pigments, natural and synthetic waxes, zinc oxide, titanium dioxide.

Other examples of suitable benefit agents include: depigmentation agents; reflectants; UV absorbers, thickening agents; detangling/wet combing agents; film forming polymers; humectants; amino acids and their derivatives; antimicrobial agents; anti-acne agents; anti-aging agents; antiseptics; analgesics; local anesthetics; anti-hair loss agents; hair growth inhibitor agents; inflammation inhibitors; proteins; deodorants and anti-perspirants; agents for treatment of dandruff, seborreheic dermatitis and psoriasis; skin emollients and skin moisturizers; hair conditioners; hair softeners; hair moisturizers; vitamins; tanning agents; skin lightening agents; antifungals such as antifungals for foot preparations; depilating agents; counterirritants; hemorrhoidals; insecticides; pigments or opacifying agents, moisturizing beads, natural abrasives, synthetic abrasives such as polyoxyethylene beads, mineral oils, petrolatum, silicone oils, polyalkylsiloxanes, polyalkyarylsiloxanes, sunscreens, reflectants and the like; and mixtures thereof.

Examples of suitable reflectants include mica, alumina, calcium silicate, glycol dioleate, glycol distearate, silica, sodium magnesium fluorosilicate, and mixtures thereof.

Examples of suitable UV absorbers include benzophenone, bornelone, PABA (Para Amino Benzoic Acid), butyl PABA, cinnamidopropyl trimethyl ammonium chloride, disodium distyrylbiphenyl disulfonate, potassium methoxycinnamate, and mixtures thereof.

The benefit agent (or benefit agents, in total) is preferably present in amount of from 0.1 to 50%, preferably from 1 to 40%, preferably from 1.5 to 30%, and most preferably from 2 to 20% by weight based on the composition weight.

A structurant may be added to the phase comprising the surface active agent, suitably in an amount of from 0.01%, preferably from 0.1%, more preferably from 1%, by weight based on the composition weight.

A structurant may be added to the phase comprising the surface active agent, suitably in an amount of up to 15%, preferably up to 12%, more preferably up to 10%, and most preferably up to 5%, by weight based on the composition weight.

The primary purpose of a structurant is to assist in the formation of a lamellar phase. It is believed that a lamellar phase, if achieved, may enable the compositions to suspend particles more readily while still maintaining good shear thinning properties. The lamellar phase also provides consumers with desired rheology ("heaping").

Suitable structurants include swelling clays, for example laponite; fatty acids and derivatives thereof, in particular, fatty acid esters; cross-linked polyacrylates such as Carbopol™ (polymers available from Goodrich); acrylates and copolymers thereof; polyvinylpyrrolidone and copolymers thereof; polyethylene imines; salts such as sodium chloride and ammonium sulphate; sucrose esters; gellants; and mixtures thereof. Examples of fatty acids which may be used are $C_{10}$-$C_{22}$ acid (e.g. lauric, oleic etc.), isostearic acid, linoleic acid, linolenic acid, ricinoleic acid, elaidic acid, arachidonic acid, myristoleic acid and palmitoleic acid. Ester derivatives include propylene glycol isostearate, propylene glycol oleate, glyceryl isostearate, glyceryl oleate and polyglyceryl diisostearate. Monoglyceride polyglycol ethers are suitable structurants.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The surface active agent phase may also comprise a thickening agent, ie a material which maintains the viscosity of this phase as the shear rate thereof is increased during use. Suitable materials include cross-linked polyacrylates such as Carbopol™ (polymers available from Goodrich); natural gums including alginates, guar, xanthan and polysaccharide derivatives including carboxy methyl cellulose and hydroxypropyl guar; propylene glycols and propylene glycol oleates; salts such as sodium chloride and ammonium sulphate; glycerol tallowates; and mixtures thereof.

Thickeners may also be added to the benefit agent in order to achieve the required viscosity during use. Preferred thickeners for the benefit agent include fumed silica; polyethylene; alkyl silicone waxes; aluminium silicate; lanesterol; natural and synthetic waxes; fatty acids and derivatives thereof, in particular, fatty acid monoglyceride polyglycol ethers; higher fatty alcohols; petrolatum; narogel; polyammonium stearate; hydrotalcites; and mixtures thereof. Hydrotalcites are materials of general formula

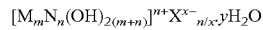

$$[M_m N_n (OH)_{2(m+n)}]^{n+} X^{x-}_{n/x} \cdot y H_2O$$

where M is a divalent metal ion e.g. $Mg^{2+}$; N is a trivalent metal ion e.g. $Al^{3+}$; X is an exchangeable anion e.g $CO_3^-$, $NO_3^-$; stearate, cinnimate; m is the number of divalent metal ions; and n is the number of trivalent metal ions.

Furthermore, the benefit agent may also function as a carrier to deliver efficacy agents to skin treated with the compositions of the invention. This route is particularly useful for delivering efficacy agents which are difficult to deposit onto the skin or those which suffer detrimental, interactions with other components in the composition. In such cases the carrier is often a silicone or hydrocarbon oil which is non solubilised/micellised by the surface active phase and in which the efficacy agent is relatively soluble. Examples of such efficacy agents include anti-viral agents; hydroxycaprylic acids; pyrrolidone; carboxylic acids; 3,4, 4'-trichlorocarbanilide; benzoyl peroxide; perfumes; essential oils; germicides and insect repellants such as 2,4,4'-trichloro-2'-hydroxydiphenyl ether (Irgasan DP300); salicylic acid; willow extract, N,N-dimethyl m-toluamide (DEET); and mixtures thereof.

The composition may contain one or more additional anionic surface-active agents, in addition to the acyl sulphonate salt defined above; preferably selected from salts of fatty acids; alkali metal salts of mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, non-acylated alkyl isethionates; fatty acid taurates; acyl taurates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids and salts of lipoamino acids. Particularly exemplary salts of the above, where applicable, are the sodium, potassium, ammonium, magnesium and triethylamine salts.

In the case of sodium lauryl ether sulfate, LESNa, this is a surface-active agent widely used in shampoos by reason of its foaming properties. It is a cheap, conventional, washing base.

The composition may contain one or more non-ionic surface-active agents, preferably selected from the following: reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl ($C_6$-$C_{22}$) phenol-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine); long chain tertiary amine oxides, long chain tertiary phosphine oxides and dialkyl sulphoxides; alkyl amido amine oxides; alkyl tertiary phosphine oxides; alkoxyl alkyl amines; sorbitan; sorbitan esters; sucrose esters; sugar amides, such as a polysaccharide amide; lactobionamides; and alkyl polysaccharide nonionic surfactants, for example alkylpolyglycosides. Preferred non-ionic surfactants are sucroglycerides and ethyoxylated fatty alcohols, especially those derived from lauryl, cetylstearyl, stearyl, cetyl and oleocetyl alcohols.

A non-ionic surface active agent, when present, preferably comprises up to 15% wt of the composition, preferably up to 10% wt.

Representative solid particles include active materials or agents such as those used for hair treatments, e.g., zinc pyrithione, or any abrasive materials which may be of natural or synthetic origin. In particular, these are polycarbonates, polypropylenes, polyethylenes, alumina, calcite and clays. Such particles generally have a crystal size ranging from about 1 to 600 microns and preferably from about 10 to 400 microns.

In the case of the suspended droplets, these are preferably droplets of at least one vegetable oil, essential oil and/or, more particularly, silicone oil.

The silicone oils which are well suited according to the present invention include the polyalkylsiloxanes, polyalkylarylsiloxanes and mixtures thereof. The preferred polyalkylsiloxanes are, especially, polydimethylsiloxanes such as dimethicone whose viscosity may range from about 20 mPa·s to 50 Pa·s at 25° C., pure or mixed with cyclomethicone. Particularly exemplary of the polyalkylarylsiloxanes are the polyphenyldimethyl-siloxanes.

In particular, polydiorganosiloxanes such as polydimethylsiloxanes having a molecular weight of less than or equal to 3,000,000 and polydimethyl-diphenylsiloxanes of molecular weight of about 600,000 are especially well suited according to the invention. The size of the oil droplets within the compositions of the invention advantageously ranges from about 0.5 to 50 microns.

The formulations according to the invention may contain approximately 0.5% to 8% and, preferably, about 1.5% to 4.5% by weight of water-insoluble particles.

Specific formulations of the invention may include these:
(a) as additional anionic agent LESNa and as co-surface-active agent lauryl alcohol containing two moles of ethylene oxide per mole of lauric alcohol and as electrolyte NaCl in a lauryl alcohol 2EO/LESNa mole ratio of from 2.1 to 4.3,
(b) as additional anionic agent, a sodium lipoamino acid and the lipoproteol LC0® mixed with the same lauryl alcohol containing two moles of ethylene oxide per mole of lauric acid and having a lauryl alcohol 2EO/sodium lipoamino acid mole ratio ranging from about 1.2 to 6.7,
(c) as additional anionic agent LESNa, and as co-surface-active agent oleylbetaine and as electrolyte NaCl, in an oleylbetaine/LESNa mole ratio of from 1.1 to 3.7.

Generally, the compositions according to the invention contain an anionic surface-active agent mixed with at least one cosurface-active agent in a cosurface-active agent/anionic surface-active agent mole ratio equal to or greater than 1.

A benefit of the invention is the ability to suspend oil and/or emollient particles in a non-Newtonian composition. The following oil/emollients may optionally be suspended in the compositions of the invention. Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: acetylated lanolin alcohols, lanolin, lard, mink oil and tallow.

Other examples of oil/emollients include mineral oil, petrolatum, silicone oil such as dimethyl polysiloxane, lauryl and myristyl lactate.

The emollient/oil is generally used in an amount from about 0 to 20%, preferably 0 to 15% by wt. of the composition.

In addition, the compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

Antimicrobials such as 2-hydroxy-4,2'4' trichloro-diphenyl-ether (DP300); preservatives, for example dimethyloldimethyl-hydantoin (Glydant XL1000), parabens, sorbic acid etc.

Coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330-Polyquaternium 39; Jellner Polyquaternium 10; Merquat 550; and Jaguar® type conditioners.

Deflocculating polymers.

Chelating agents including but not limited to EDTA, EDTA salts, NTA, methylenediamine disuccinate and salts of methylenediamine disucuccinate.

Compositions of the invention may be formulated as products for washing the skin, for example, bath or shower gels, hand washing compositions or facial washing liquids; pre- and post-shaving products; rinse-off, wipe-off and leave-on skin care products; products for washing the hair and for dental use.

In accordance with a second aspect of the present invention there is provided the use of a composition of the invention, as defined above, in the formulation of a personal care product with improved stability, in an aqueous environment.

In accordance with a third aspect of the present invention there is provided the use of a composition of the invention, as defined above, in the formulation of a personal care product which has improved stability in an aqueous environment compared with a corresponding compound in which each of $R^2$ to $R^5$ is a hydrogen atom.

Suitably the composition, and in particular the defined sulfonated compound, is resistant to breakdown in an aqueous environment. Preferably it has essentially no effect on the pH of the product, over time. It has excellent lathering properties and is very mild to skin and eyes.

Weight percentage values herein refer to the total complement of compounds of a named type, e.g. amphoteric or zwitterionic surfactants in total; or benefit agents in total.

Where a percentage value is given for a component it refers to the active content of that component.

The invention will now be further described, by way of example, with reference to the following examples.

Examples 1 to 5 were carried out to assess the suitability of certain isethionate salts for use in the present invention. Examples 6-14 relate to certain compositions which are within the scope of the present invention.

In the examples abbreviations used are as follows:
SCMI—sodium cocoylmethylisethionate
SCI—sodium cocoyl isethionate
SLS—sodium lauryl sulfate
SLMI—sodium lauroylmethylisethionate
SLES—sodium laureth sulfate
SCEI—sodium cocoyl ethyl isethionate
CAPB—cocamidopropyl betaine
CMEA—cocamide monoethanolamine.

BRIEF DESCRIPTION OF THE DRAWINGS

FIG. 3 is a plot showing skin irritancy properties of a number of compounds, including two sulfate surfactants; SLS and SLES (known to have significant irritancy), distilled water, SCI (known to have low irritancy) and SCMI, as described in Example 3.

EXAMPLE 1

In a preliminary test the stability of SCMI in 10 wt % aqueous solutions adjusted to have initial pH values respectively of 4.5, 5.5, 6.5, 7.5, 8.5 and 9.5, each held at 48.9° C. for an extended period of days, were tested for the amount of SCMI present over the test period.

The pH values were read using a standard electrode pH meter (Fisher Accument XL-25). The electrode was place in the composition (no further dilution) and the pH recorded.

Figure 1:
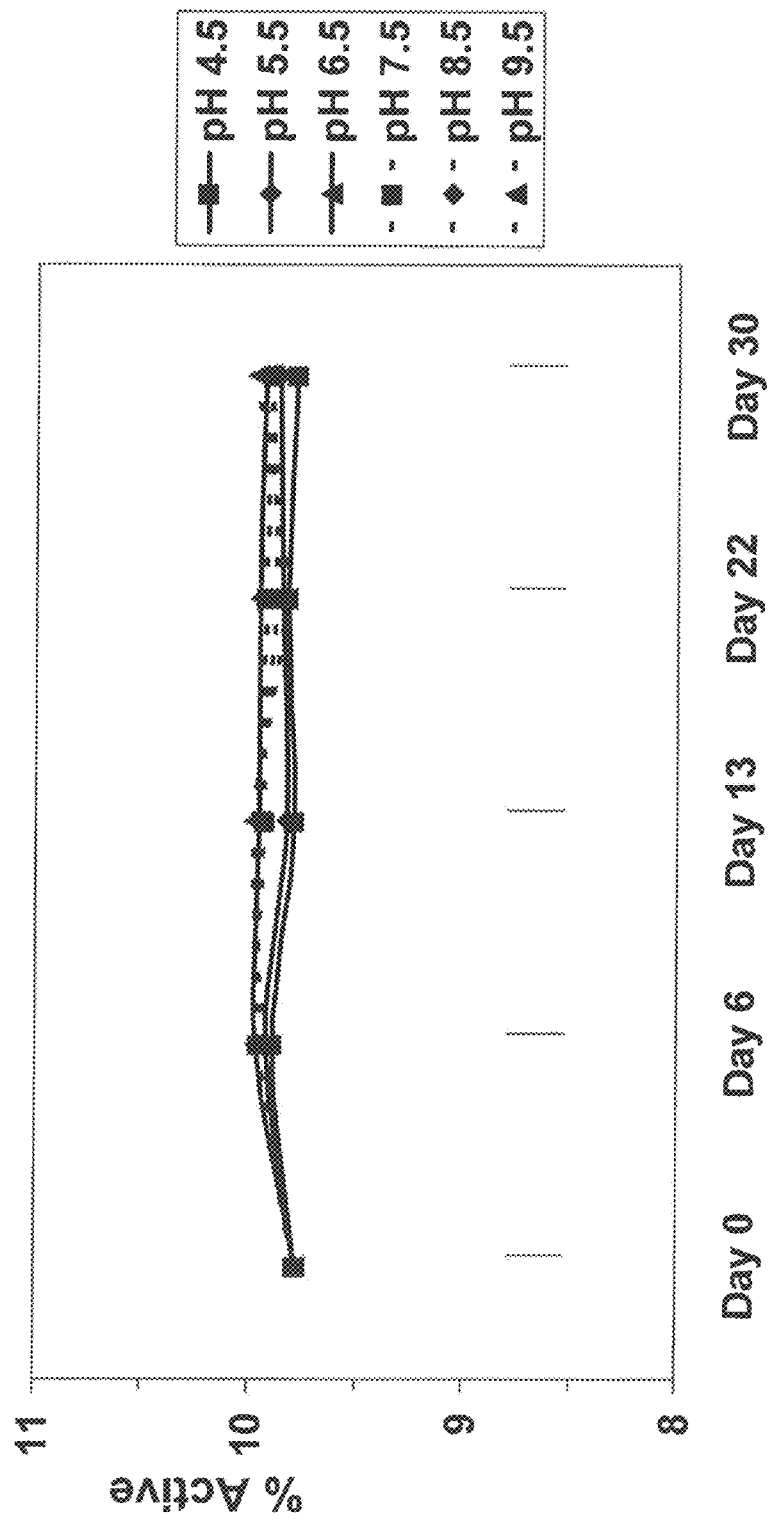
FIG. 1 is a plot showing the amount of sodium cocoylmethylisethionate (SCMI) present in aqueous solutions having various pH values following incubation at 48.9° C. at various intervals over a 30 day period of time.

The results are shown in FIG. 1. It can be seen that the percentage of SCMI does not change from Day 0 to Day 30, at any of these pH values.

EXAMPLE 2

In a preliminary test 10 wt % solutions of SCMI, adjusted to have initial pH values respectively of 4.5, 5.5, 6.5, 7.5, 8.5 and 9.5, each held at 48.9° C. for an extended period of days, were tested for their pH stability over the extended period. The pH testing was as described above.

Figure 2:
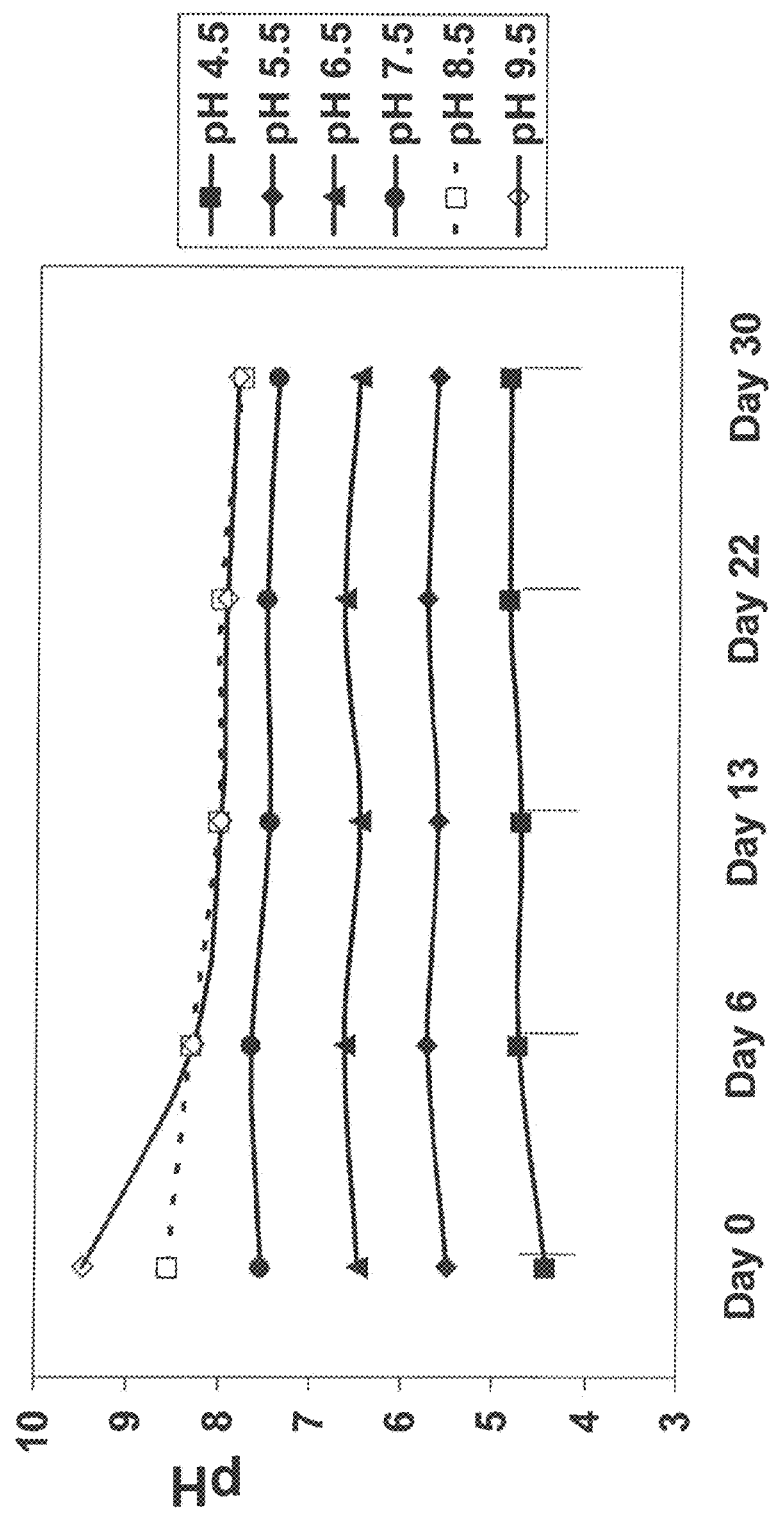
FIG. 2 is a plot showing the pH stability of sodium cocoylmethylisethionate (SCMI) present in aqueous solutions having various pH values following incubation at 48.9° C. at various intervals over a 30 day period of time.

The results are shown in FIG. 2. It can be seen that the pH values were substantially unchanged from Day 0 to Day 30 at all these pH values, except for a small pH reduction in the first few days, for the sample held at the highest pH value, 9.5.

EXAMPLE 3

In a preliminary test based on the Zein protocol the skin irritancy properties of a number of compounds were tested, including two sulfate surfactants SLS and SLES (known to have significant irritancy), distilled water, SCI (known to have low irritancy) and SCMI. The results are shown in FIG. 3. SCMI and SLMI were shown to have low irritancy, similar to that shown by SCI; and significantly lower than the sulfates.

The Zein protocol is an in-vitro test to measure skin irritancy of formulations. The method makes use of the correlation between binding ability of surfactants to proteins and the damage the surfactant causes to the skin. The de-naturation of epidermal protein is a key mechanism in the development of observable damage to the skin by surfactants. Zein protein, an insoluble protein extracted from corn kernel, is used as a model for epidermal protein and the solubility of the Zein protein in surfactant solutions is believed to be a reliable guide for the skin irritancy caused by the surfactant. The test involves establishing the amount of Zein protein which can be solubilised by surfactant. 5 g of Zein protein may be dispersed in 40 $cm^3$ of surfactant solution (at 2 wt % concentration). The mixture is shaken for 1 hour at 35° C., and immediately centrifuged to remove any non-solubilised Zein. The amount solubilised is estimated from the solution nitrogen content using micro-Kjeldahl method (making allowance for any nitrogen in the compound tested).

EXAMPLE 4

Simple solubility tests were carried out.

10 wt % of SCI shaken with deionised water gave a milky white suspension. The solubility limit of SCI in water is quoted as 0.5 wt %.

10 wt % of SCMI added to deionised water immediately gave a clear solution.

10 wt % of SCEI added to deionised water immediately gave a clear solution.

EXAMPLE 5

Foaming tests were performed using a capped measuring cylinder which was charged with an aliquot of the stated surfactant leaving room for foam to form. Foam heights in the graduated cylinder were measured at the start and after 10 inversions of the cylinder. The operation was carried out in the same manner for each surfactant.

100% SLES gave a foam of medium height but which was also open and "watery".

80 wt % SLS/20 wt % CAPB gave a foam which was high but open and "watery".

100% SCMI gave a foam of medium height but which was rich and creamy.

80% SCMI/20% CAPB gave a foam of medium height but which was rich and creamy.

EXAMPLES 6 TO 14

Formulated compositions containing canola oil as benefit agent were prepared and tested for viscosity and physical stability over a one-month period. The results are set out in the table below.

|  | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|
| Water | 51.6 | 50.6 | 49.6 | 48.6 | 66.66 | 49.6 | 49.6 | 45.35 | 42.85 |
| NTRLQUEST E-30 (formerly OCTAQUEST E-30) | 1 | 1 | 1 | 1 |  | 1 | 1 |  |  |

-continued

| | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|
| Tetrasodium EDTA (40%) | | | | | | | | 0.25 | 0.25 |
| FINSOFT C-17 | 0.4 | 0.4 | 0.4 | 0.4 | | 0.4 | 0.4 | 0.4 | 0.4 |
| Cocamidopropyl betaine (30%) | | | | 12.5 | 16.67 | 12.5 | 12.5 | 12.5 | 12.5 |
| Sodium Lauroamphoacetate | 12.5 | 12.5 | 12.5 | | | | | 5 | 7.5 |
| SCMI (85%) | 15 | 15 | 15 | 15 | 6.17 | 15 | | | |
| SLMI (85%) | | | | | | | 15 | 15 | 15 |
| Cocamide MEA | 3.5 | 3.5 | 3.5 | 3.5 | | 3.5 | 3.5 | 3.5 | 3.5 |
| Canola oil | 12 | 12 | 12 | 12 | 2.5 | 12 | 12 | 12 | 12 |
| Sodium chloride | 3 | 4 | 5 | 6 | 8 | 5 | 5 | 5 | 5 |
| 50% citric acid solution (to pH 5-6) | 1 | 1 | 1 | 1 | | 1 | 1 | 1 | 1 |

NTRLQUEST, OCTAQUEST, FINSOFT are registered trade marks of Innospec
Brookfield RVT Viscometer Heleopath T-Bar Spindles @ 25° C.

| | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|
| T-Bar Spindle B @ 1 RPM | 14,800 | 18,000 | 27200 | 37200 | | | | | |
| T-Bar Spindle B @ 2.5 RPM | 8320 | 9600 | 13,760 | 18400 | | | | | |
| T-Bar Spindle C @ 1 RPM | | | | | 17000 | 60000 | 56000 | 77000 | 77000 |
| T-Bar Spindle C @ 2.5 RPM | | | | | 20400 | 28400 | 28000 | 37200 | 36400 |
| Appearance | White Lotion | White Lotion | White Lotion | White Lotion | White Lotion | White Lotion | White Lotion | White Lotion | White Lotion |
| Stability over 1 month test period | Stable | Stable | Stable | Stable | Stable | Stable | Stable | Stable | Stable |

The formulations of Examples 15 and 16 were prepared by progressive mixing and blending of the components, in the order given. The pH was adjusted to between 5.2 and 5.8 using citric acid after blending of the preceding components (in the respective tables), but before blending in of the fragrance, dye and preservative.

EXAMPLE 15

The following moisturizing and conditioning shampoo was prepared.

| Ingredients | Tradename (Supplier) | % w/w |
|---|---|---|
| Water | | to 100 |
| Trisodium Ethylenediamine disuccinate | Natrlquest E30 (Innospec) | 0.15 |
| Sodium Chloride | | 4.00 |
| Guar Hydroxypropyltrimonium Chloride | Activsoft C-17 (Innospec) | 0.2 |
| Disodium Cocoamphodipropionate | Miranol C2M Conc. (Rhodia) | 7.5 |
| Sodium Methyl Cocoyl Taurate | Pureact WS Conc. (Innospec) | 7.5 |
| Guar Gum | Activsoft S (Innospec) | 0.5 |
| Glycerin | | 1.00 |
| SLMI | Pureact SLMI-85 (Innospec) | 12.5 |
| Cocamide MEA | Aminol CM Flakes (Innospec) | 3.5 |
| Quaternium 75 | Condicare CT (Innospec) | 2.00 |
| Dimethicone | Dow Corning 200 Fluid (Dow Corning) | 4.00 |
| Cocamidopropyl Betaine | Mirataine BET C-30 (Rhodia) | 10.00 |
| Citric Acid (50% soln) | | pH 5-2-5.8 |
| Preservative | | trace |
| Fragrance | | trace |
| Dye(s) | | trace |

The viscosity of the conditioning shampoo of Example 15 was tested under different shear rates, on a viscometer with a T-Bar C Spindle, at 22° C. The results were as follows:

0.5 RPM=160,000 cps
1.0 RPM=90,000 cps
2.5 RPM=42,400 cps

EXAMPLE 16

The following foaming body lotion was prepared.

| Ingredients | Tradename (Supplier) | % w/w to 100 |
|---|---|---|
| Water | | to 100 |
| Trisodium Ethylenediamine disuccinate | Natrlquest E30 (Innospec) | 0.15 |
| Sodium Chloride | | 3.6 |
| Guar Hydroxypropyltrimonium Chloride | Activsoft C-17 (Innospec) | 0.18 |
| Disodium Cocoamphodipropionate | Miranol C2M Conc. (Rhodia) | 6.7 |
| Sodium Methyl Cocoyl Taurate | Pureact WS Conc. (Innospec) | 6.7 |
| Guar Gum | Activsoft S (Innospec) | 0.45 |
| Glycerin | | 1.00 |
| SLMI | Pureact SLMI-85 (Innospec) | 11.2 |
| Cocamide MEA | Aminol CM Flakes (Innospec) | 3.1 |
| Canola Oil | Rita Canola Oil (Rita) | 9.00 |
| Cocamidopropyl Betaine | Mirataine BET C-30 (Rhodia) | 10.00 |
| Trideceth-7 Carboxylic Acid | Pureact TA (Innospec) | 3.5 |
| Citric Acid (50% soln) | | to pH 5.2-5.8 |
| Preservative | | trace |
| Fragrance | | trace |
| Dye(s) | | trace |

The viscosity of the foaming body lotion of Example 16 was tested under different shear rates, on a viscometer with a T-Bar C Spindle, at 22° C. The results were as follows:

0.5 RPM=240,000 cps
1.0 RPM=140,000 cps
2.5 RPM=64,000 cps

The invention claimed is:

1. An aqueous, shear thinning personal care composition comprising:
   (a) at least 3 wt % of a sulfonate compound of general formula:

$$R^1\underset{O}{\overset{\phantom{O}}{C}}-O-\underset{R_3}{\overset{R_2}{C}}-\underset{R_5}{\overset{R_4}{C}}-SO_3^- \quad M^+$$

where
   $R_1$ represents a $C_{8-22}$ alkyl group;
   $R_2$ represents a $C_{1-4}$ alkyl group; and
   each of $R_3$, $R_4$ and $R_5$ independently represents a hydrogen atom or a $C_{1-4}$ alkyl group; and
   $M^+$ represents a cation;
   (b) at least 3 wt % of an amphoteric or zwitterionic surfactant;
   (c) at least 10 wt % of water;
   (d) from about 0.1% to about 50% wt % of an additional component in the form of solid or non-solid water-insoluble particles or droplets suspended in the composition;
   (e) an electrolyte present in an amount from 2 wt % to 25 wt %; and
   wherein said composition is capable of maintaining said solid or non-solid water-insoluble particles or droplets in suspension without sedimentation or separation over a time period of at least one month, and
   wherein the composition does not comprise an additional structurant.

2. The composition as claimed in claim 1 wherein $R_2$ represents a methyl group.

3. The composition as claimed in claim 1 wherein each of $R_3$, $R_4$ and $R_5$ represents a hydrogen atom.

4. The composition as claimed in claim 1 wherein component (a) is present in an amount of up to 30 wt %.

5. The composition as claimed in claim 1 wherein component (b) is present in an amount of up to 30 wt %.

6. The composition as claimed in claim 1 wherein component (c) is present in an amount of from 20% to 95% by total composition weight.

7. The composition as claimed in claim 1 wherein component (d) is present in an amount from at least 0.5 wt %.

8. The composition as claimed in claim 1, wherein said additional component (d) is a benefit agent.

9. The composition as claimed in claim 1, wherein the composition further includes a benefit agent.

10. The composition as claimed in claim 1, formulated as a product selected from the following: a bath or shower gel; a hand washing composition; a facial washing composition; a pre-, during- or post-shaving product; a skin moisturizer; a hair gel; a medicinal skin treatment product; a shampoo; a hair conditioner; a dental product.

11. The composition as claimed in claim 1, wherein said electrolyte is present in an amount up to 15 wt %.

12. The composition as claimed in claim 1, wherein said electrolyte is present in an amount up to 10 wt %.

13. A personal care composition comprising:
   a) a viscous, shear-thinning component consisting essentially of water and
      (i) at least 3 wt % of a sulfonate compound of general formula:

$$R^1\underset{O}{\overset{\phantom{O}}{C}}-O-\underset{R_3}{\overset{R_2}{C}}-\underset{R_5}{\overset{R_4}{C}}-SO_3^- \quad M^+$$

where
   $R_1$ represents a $C_{8-22}$ alkyl group;
   $R_2$ represents a $C_{1-4}$ alkyl group; and
   each of $R_3$, $R_4$ and $R_5$ independently represents a hydrogen atom or a $C_{1-4}$ alkyl group; and
   $M^+$ represents a cation;
      ii) at least 3 wt % of an amphoteric and/or zwitterionic surfactant component;
      iii) from 2 wt % to 25 wt % of an electrolyte component; and
      iv) from about 0.1 wt % to about 50 wt % of an additional component in the form of solid or non-solid water-insoluble particles or droplets suspended in the composition;
   wherein said composition maintains said solid or non-solid water-insoluble particles or droplets in suspension without sedimentation or separation over a time period of at least one month, and
   wherein the composition does not comprise an additional structurant.

14. The composition as claimed in claim 13 wherein $R_2$ represents a methyl group.

15. The composition as claimed in claim 14 wherein each of $R_3$, $R_4$ and $R_5$ represents a hydrogen atom.

16. The composition as claimed in claim 13, wherein said additional component comprises a benefit agent.

17. The composition as claimed in claim 13, wherein the composition further comprises a benefit agent.

18. The composition as claimed in claim 13, formulated as a product selected from the following: a bath or shower gel; a hand washing composition; a facial washing composition; a pre-, during- or post-shaving product; a skin moisturizer; a hair gel; a medicinal skin treatment product; a shampoo; a hair conditioner; a dental product.

* * * * *